United States Patent
Drobyshev et al.

(10) Patent No.: US 11,267,771 B2
(45) Date of Patent: Mar. 8, 2022

(54) METHOD FOR SEPARATING NON-LINEAR OLEFINS FROM AN OLEFIN FEED BY REACTIVE DISTILLATION

(71) Applicants: IFP Energies Nouvelles, Rueil-Malmaison (FR); Total Research & Technology Feluy, Seneffe (BE)

(72) Inventors: Kirill Drobyshev, Rueil-Malmaison (FR); Vincent Coupard, Rueil-Malmaison (FR); Nikolai Nesterenko, Nivelles (BE)

(73) Assignees: IFP Energies Nouvelles, Rueil-Malmaison (FR); Total Research & Technology Feluy, Seneffe (BE)

(*) Notice: Subject to any disclaimer, the term of this patent is extended or adjusted under 35 U.S.C. 154(b) by 33 days.

(21) Appl. No.: 16/968,186

(22) PCT Filed: Jan. 28, 2019

(86) PCT No.: PCT/EP2019/051942
§ 371 (c)(1),
(2) Date: Aug. 7, 2020

(87) PCT Pub. No.: WO2019/154645
PCT Pub. Date: Aug. 15, 2019

(65) Prior Publication Data
US 2021/0371360 A1 Dec. 2, 2021

(30) Foreign Application Priority Data
Feb. 9, 2018 (FR) ........................ 1851134

(51) Int. Cl.
*C07C 7/04* (2006.01)
*C07C 7/148* (2006.01)
(Continued)

(52) U.S. Cl.
CPC .......... *C07C 7/14891* (2013.01); *B01D 3/009* (2013.01); *B01D 3/4205* (2013.01); *C07C 1/24* (2013.01); *C07C 7/04* (2013.01)

(58) Field of Classification Search
CPC ......... C07C 41/42; C07C 41/06; C07C 11/08; C07C 11/02; C07C 5/2506; C07C 11/06;
(Continued)

(56) References Cited

U.S. PATENT DOCUMENTS

| 4,307,254 A | 12/1981 | Smith |
| 5,248,836 A | 9/1993 | Bakshi et al. |

(Continued)

FOREIGN PATENT DOCUMENTS

| DE | 102006057856 A1 | 6/2008 |
| EP | 0755706 B1 | 12/2006 |

(Continued)

OTHER PUBLICATIONS

International Search Report PCT/EP2019/051942 dated Mar. 6, 2019 (pp. 1-6).

*Primary Examiner* — Sharon Pregler
(74) *Attorney, Agent, or Firm* — Millen, White, Zelano and Branigan, P.C.; Harry Shubin

(57) ABSTRACT

The present invention relates to a process for treating, by reactive distillation, an olefinic feedstock comprising linear olefins containing n carbon atoms, and branched olefins, the branched olefins comprising tertiary branched olefins, for example a mixture of n-butenes and of tertiary branched olefins comprising isobutene, so as to produce an olefinic effluent with a mass content of tertiary branched olefin of less than or equal to 3% by weight and a heavy hydrocarbon effluent, said process comprising the feeding of a reactive distillation section with said olefinic feedstock and with an alcohol feedstock comprising a primary alcohol, said reac- (Continued)

tive distillation section comprising a column composed at least of an upper reflux zone into which is introduced said alcohol feedstock, comprising, for example, ethanol, an intermediate reaction zone comprising at least 6 reactive doublets, and a lower fractionation zone at the level of which said section is fed with said olefinic feedstock, said reactive distillation section being operated at a relative pressure of between 0.3 and 0.5 MPa, a column head temperature of between 40° C. and 60° C., with a reflux ratio of between 1.8 and 2.2.

14 Claims, 1 Drawing Sheet

(51) Int. Cl.
*B01D 3/42* (2006.01)
*B01D 3/00* (2006.01)
*C07C 1/24* (2006.01)

(58) Field of Classification Search
CPC .. C07C 11/09; B01D 3/009; B01J 8/02; B01J 8/048; B01J 8/0469
See application file for complete search history.

(56) References Cited

U.S. PATENT DOCUMENTS

| | | | |
|---|---|---|---|
| 5,368,691 A | | 11/1994 | Asselineau et al. |
| 5,498,318 A | | 3/1996 | Alagy et al. |
| 5,776,320 A | * | 7/1998 | Marion ............ B01D 3/009 203/29 |
| 7,473,812 B2 | | 1/2009 | Peters et al. |
| 9,260,355 B2 | | 2/2016 | Vermeiren et al. |

FOREIGN PATENT DOCUMENTS

| | | |
|---|---|---|
| EP | 2547639 B1 | 8/2016 |
| FR | 2675055 A1 | 10/1992 |
| WO | 9408927 A1 | 4/1994 |
| WO | 11113834 A1 | 9/2011 |

\* cited by examiner

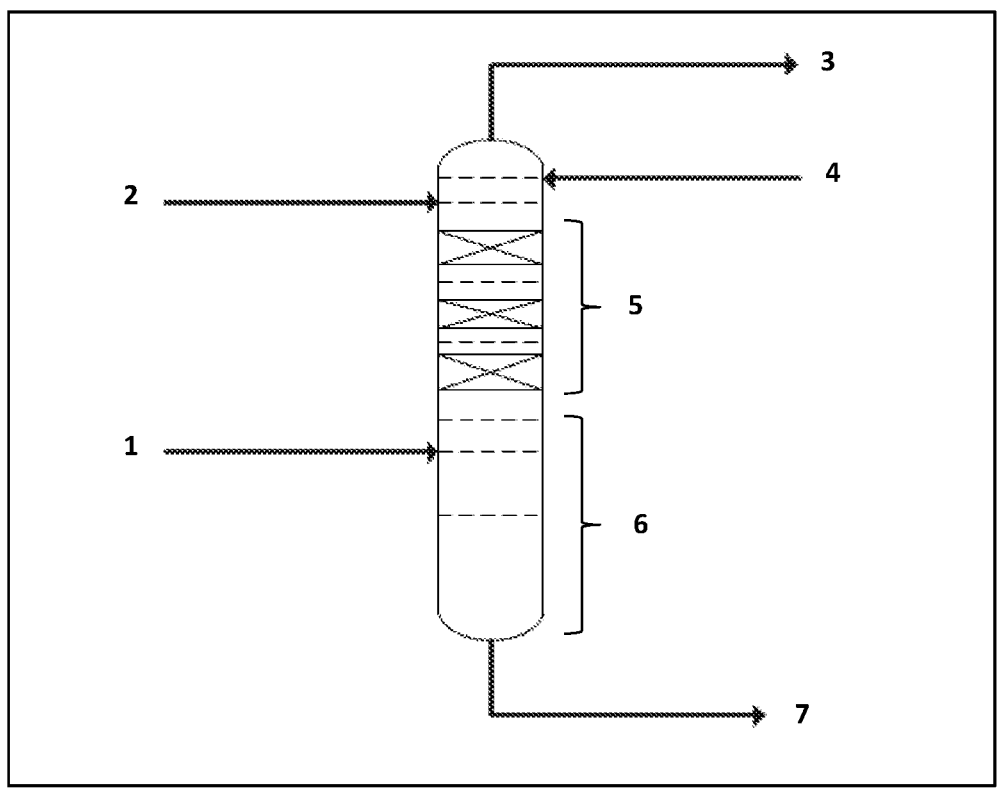

METHOD FOR SEPARATING NON-LINEAR OLEFINS FROM AN OLEFIN FEED BY REACTIVE DISTILLATION

TECHNICAL FIELD OF THE INVENTION

The present invention relates to a process for treating, by reactive distillation, an olefinic feedstock so as to produce an olefinic effluent essentially comprising linear olefins, of the desired chain length, and tertiary branched olefins in a content of less than or equal to 3% by weight. Advantageously, the present invention applies to an olefinic feedstock comprising a mixture of n-butenes (1-butene, 2-butenes) and of isobutene, to produce an effluent with an isobutene content of less than or equal to 3% by weight.

The present invention also relates to a process for the isomerizing dehydration of alcohols to olefins, the conversion of the alcohol to olefins advantageously being performed on a zeolite catalyst of FER type, preferably with an Si/Al mole ratio of less than 100, comprising an improved step of treating the olefinic raffinate produced so as to obtain an effluent essentially comprising linear olefins with a content of tertiary branched olefins of less than or equal to 3% by weight.

The olefinic effluent obtained, essentially comprising the targeted linear olefins, has the advantage of being able to be used as reagent in a metathesis reaction.

PRIOR ART

WO 2011/113834 describes the simultaneous dehydration and backbone isomerization of isobutanol. The maximum achieved proportion of n-butenes in the raffinate is 58.4% at 375° C. at a high WHSV (12.6 h$^{-1}$) on a powdered FER zeolite with an Si/Al of 33. According to WO 2011/113834, such a mixture may be used, for example, for the conversion of isobutene into ethers, tert-butyl alcohol or oligomers or for the transformation of n-butenes in metathesis reactions. As regards the methods for separating isobutene from the n-butenes, WO 2011/113834 mentions catalytic distillation consisting in isomerizing the 1-butene into 2-butene, which is heavier, and in separating it out by distilling off the 2-butene which is extracted at the bottom of the column and the isobutene exiting at the top of the column. However, WO 2011/113834 does not give any indication regarding the quality of the isobutene/2-butene separation. In particular, WO 2011/113834 does not give any indication regarding the composition of the 2-butene effluent and the yields of n-butenes recovered after this catalytic distillation.

Patent EP 2 547 639 specifies that n-butenes may be used in metathesis when the olefinic stream comprises less than 10% by weight, preferably less than 5% by weight, of isobutene. To remove the isobutene and achieve this specification, EP 2 547 639 proposes the isobutene conversion and separation methods mentioned in document WO 2011/113834 (oligomerization, etherification, hydration to alcohol, catalytic distillation with conversion of the 1-butene to 2-butene and simultaneous separation of the 2-butene).

U.S. Pat. No. 7,473,812 discloses a method for removing isobutene from a mixture of butene isomers (n-butenes and isobutene) which consists of a first step of oligomerization of the isobutene and then a second step of etherification of the remaining isobutene (representing about 10% by weight of the raffinate obtained from the first step) with an alcohol, for example ethanol, on an acid catalyst. The etherification step more precisely consists of the succession of an etherification of the remaining isobutene in a reactor under the thermodynamic conditions followed by a reactive distillation to convert the residual isobutene representing only 0.57% by weight of the effluent obtained from the thermodynamic reactor into ether and separating out the ether formed, in a column comprising an upper rectification zone, an intermediate reactive zone and a lower fractionation zone, at a pressure adjusted to 7.5 bar.

U.S. Pat. No. 5,368,691 discloses, for its part, a method for the reactive distillation of a feedstock obtained from an etherification reactor, comprising isobutene (about 5% by weight), linear butenes, methanol and methyl tert-butyl ether (MTBE), so as to improve the overall yield of the ether MTBE. The reactive distillation column comprises an upper rectification zone comprising 7 theoretical plates, an intermediate reactive zone comprising a sulfonic resin as catalyst, and a lower fractionation zone. The column is operated at a pressure of 8 bar, a reflux of 1:1, a column head temperature of 67° C. and a column bottom temperature of 140° C. A methanol supplement may be added at the level of the first reactive plate.

Patent FR 2 675 055 describes an MTBE synthesis process comprising a reactive column fed with a feedstock containing methanol and a mixture of butenes and butanes containing about 5% isobutene, at a pressure of 0.5 MPa and a temperature of between 60 and 80° C., the feedstock being obtained from a first conversion step during which the isobutene of the feedstock (about 25%) is 80% converted into MTBE. This method allows a conversion of the order of 80% of the residual isobutene.

Patent EP 0 755 706 also describes a reactive distillation method for improving the conversion of isobutene into the ether MTBE. The reactive distillation column is fed with a feedstock obtained from a first etherification reaction section and still comprising 2.7% by weight of isobutene. The column comprises an upper rectification zone with 8 theoretical plates, an intermediate reactive zone with 5 catalytic beds comprising a sulfonic resin, and a lower fractionation zone. The column is operated at a relative pressure of 0.7 MPa, with a reflux ratio of 1:1 and a temperature profile ranging from 62° C. at the head to 139° C. at the bottom.

However, none of the prior art documents explains how to treat an olefinic feedstock comprising at least 10% by weight of tertiary branched olefins, such as isobutene, to obtain an olefinic effluent essentially comprising linear olefins with a content of tertiary branched olefins of less than or equal to 3% by weight so as to comply with the specifications for a metathesis feedstock. In particular, no mention is made of a method for treatment, by reactive distillation, of a feedstock obtained from the dehydration of alcohol to olefins making it possible to obtain an olefinic effluent with a content of tertiary branched olefins of less than or equal to 3% by weight. For example, no mention is made of a method for treatment, by reactive distillation, of a feedstock obtained from the dehydration of isobutanol to butenes making it possible to obtain an olefinic effluent with a content of the combination consisting of isobutene and of tertiary branched olefins containing 5 carbon atoms of less than or equal to 3% by weight relative to the total weight of the olefinic effluent.

The Applicant has discovered that the separation and etherification of the tertiary branched olefins of the olefinic feedstock in a reactive distillation column under particular conditions, notably the localization and the amount of the feed of alcohol feedstock, the pressure, the temperature and the reflux ratio, makes it possible to achieve a sufficiently low concentration of tertiary branched olefins in the olefinic effluent at the head to be able to use this olefinic effluent in a metathesis reaction, for limited losses of alcohol and for a reasonable cost. Specifically, the Applicant has found that the treatment of the olefinic feedstock by reactive distillation, using an etherification reaction, under particular conditions, makes it possible to comply with the specifications imposed by metathesis which demands a content of less than or equal to 3% by weight of tertiary branched olefins in the olefinic feedstock to be transformed.

Subject and Advantage of the Invention

The invention relates to a process for treating, by reactive distillation, an olefinic feedstock comprising linear olefins containing n carbon atoms, n being an integer between 4 and 10, and branched olefins, the branched olefins comprising tertiary branched olefins, so as to produce an olefinic effluent with a mass content of tertiary branched olefins of less than or equal to 3% by weight and a heavy hydrocarbon effluent, said heavy hydrocarbon effluent being an effluent containing at least 50% by weight of hydrocarbons comprising more than n carbon atoms, said process comprising the feeding of a reactive distillation section with said olefinic feedstock and the feeding of said reactive distillation section with an alcohol feedstock, said alcohol feedstock comprising at least one primary alcohol, characterized in that:

said reactive distillation section comprises a column comprising a column head reflux zone, an intermediate reaction zone comprising at least 6 reactive doublets, each reactive doublet comprising a catalytic bed followed by a separating theoretical plate, and a lower fractionation zone comprising between 5 and 25 theoretical plates, said reactive distillation section is operated at a relative column head pressure in the reflux zone of between 0.3 and 0.5 MPa, a column head temperature in the reflux zone of between 40° C. and 60° C. and a molar reflux ratio of between 1.8 and 2.2, said distillation section is fed with said olefinic feedstock in the fractionation zone of said column and with alcohol feedstock in the reflux zone, such that the mole ratio of the primary alcohol introduced relative to the tertiary branched olefins, having a number of carbon atoms of less than or equal to (n+1), of the olefinic feedstock is between 0.8 and 1.1.

The invention advantageously applies to the treatment of the effluent obtained from the isomerizing dehydration of alcohols, preferably of monoalcohols, substituted in position 2 with an alkyl group and the hydroxyl group —OH of which is borne by a primary carbon atom. In particular, the invention applies to the treatment of the effluent obtained from the isomerizing dehydration, advantageously on a zeolite catalyst of FER type preferably with an Si/Al mole ratio of less than 100, of isobutanol alone or as a mixture with other butanol isomers.

Thus, the invention relates more particularly to a process for treating, by reactive distillation, an olefinic feedstock comprising a mixture of linear butenes and of branched olefins comprising tertiary branched olefins, preferably comprising at least 70% by weight of said mixture and preferably comprising at least 10% by weight of tertiary branched olefins, so as to produce an olefinic effluent, comprising having a mass content of tertiary branched olefins of less than or equal to 3% by weight and a heavy hydrocarbon effluent, said heavy hydrocarbon effluent being an effluent containing at least 50% by weight of hydrocarbons comprising more than 4 carbon atoms, said process comprising the feeding of a reactive distillation section with said olefinic feedstock and the feeding of said reactive distillation section with an alcohol feedstock, said alcohol feedstock comprising at least one primary alcohol, characterized in that:

said reactive distillation section comprises a column comprising a column head reflux zone, an intermediate reaction zone comprising at least 6 reactive doublets, each reactive doublet comprising a catalytic bed followed by a separating theoretical plate, and a lower fractionation zone comprising between 5 and 25 theoretical plates, said reactive distillation section is operated at a relative column head pressure in the reflux zone of between 0.3 and 0.5 MPa, a column head temperature in the reflux zone of between 40° C. and 60° C. and a molar reflux ratio of between 1.8 and 2.2, said reactive distillation section is fed with said olefinic feedstock in the fractionation zone and with an alcohol feedstock, comprising a primary alcohol, in the reflux zone so that the mole ratio of said primary alcohol introduced relative to the isobutene and the tertiary branched olefins containing 5 carbon atoms of the olefinic feedstock is between 0.8 and 1.1.

The invention also relates to a process for the isomerizing dehydration of a feedstock comprising from 40% to 100% by weight of alcohol substituted in position 2 with an alkyl group and the hydroxyl group —OH of which is borne by a primary carbon atom, said process comprising at least one step of converting said substituted alcohol into olefin and a step involving the process for treating, according to the invention, the olefinic raffinate produced in the conversion step.

Advantageously, the process according to the invention makes it possible to obtain, from an olefinic feedstock comprising at least 10% by weight of tertiary branched olefins, an olefinic effluent which meets the specifications for a feedstock feeding a metathesis unit. Thus, the process according to the invention makes it possible to obtain an olefinic effluent with a content of tertiary branched olefins of less than or equal to 3% by weight. Preferably, the olefinic effluent essentially comprises linear olefins, advantageously corresponding to the alcohol(s) substituted in position 2 with an alkyl group and the hydroxyl groups —OH of which are borne by primary carbon atoms, alcohol(s) from which they are obtained, and the corresponding tertiary branched olefins in a content of less than or equal to 3% by weight. More particularly, the invention makes it possible to obtain a butene effluent essentially comprising linear butenes (1-butene and 2-butenes), i.e. at least 70% by weight of linear butenes, and comprising a content of less than or equal to 3% by weight of tertiary branched olefins, notably of the combination of isobutene and tertiary branched olefins containing 5 carbon atoms.

The process according to the invention makes it possible to achieve the specifications in terms of content of tertiary branched olefins, i.e. an olefinic effluent with a content of less than or equal to 3% by weight in particular of targeted tertiary branched olefins, for limited losses of primary alcohol, introduced into the process according to the invention to allow the etherification reaction. The low content of tertiary branched olefins is also achieved for a limited cost.

Another advantage of the process according to the invention lies in the separation of the olefins, which are preferably linear, of the desired chain length (number of carbon atoms), from the hydrocarbon impurities and/or the water that may be included in the feedstock to be treated.

DETAILED DESCRIPTION OF THE INVENTION

According to the invention, the term "olefinic feedstock" means a feedstock comprising at least 70% by weight, preferentially at least 80% by weight and even more preferably at least 90% by weight of olefins, preferably of targeted olefins.

According to the invention, the term "olefinic effluent" or "olefinic effluent essentially comprising linear olefins" means the effluent extracted at the column head comprising at least 70% by weight, preferentially at least 80% by weight and even more preferably at least 90% by weight of linear olefins, preferably of targeted linear olefins, and a content of less than or equal to 3% by weight of the tertiary branched olefins, preferably of the targeted tertiary branched olefins. The olefinic effluent extracted at the top of the reactive distillation column may contain water.

According to the invention, the targeted olefins, included in the feedstock to be treated and the olefinic effluent, are olefins containing n carbon atoms, n being an integer between 4 and 10, preferably between 4 and 8 and very preferably between 4 and 5. Very preferably, the targeted linear olefins are linear butenes (1-butene and 2-butene) and the corresponding tertiary branched olefin is isobutene.

According to the invention, the tertiary branched olefins are olefins in which at least one of the carbon atoms forming part of a double bond is tertiary. The tertiary branched olefins have the property of reacting in the etherification reaction. They may form an ether after reaction with an alcohol.

The term "hydrocarbon effluent" means an effluent comprising at least 50% by weight, preferably at least 70% by weight, of hydrocarbons comprising more than n carbon atoms, n having the abovementioned definition.

According to the invention, the numbering of the theoretical plates and the positioning of the various elements in the column (such as "upstream"/"downstream") are performed in the direction of flow of the liquid in the column, i.e. from the top to the bottom of the column.

According to the invention, the term "losses of primary alcohol", for example ethanol, generally expressed as weight percentages (weight %), means the weight ratio of the total amounts (by weight) of primary alcohol found in the top olefinic effluent and in the bottom hydrocarbon effluent relative to the amounts (by weight) of primary alcohol introduced.

According to the present invention, the expression "between . . . and . . . " means that the limit values of the interval are included in the described range of values. If such were not the case and if the limit values were not included in the described range, such a clarification would be given by the present invention.

The present invention consists of a process for treating, by reactive distillation, an olefinic feedstock comprising linear olefins containing n carbon atoms, n being an integer between 4 and 10, and branched olefins, the branched olefins comprising tertiary branched olefins, so as to produce an olefinic effluent with a mass content of tertiary branched olefins of less than or equal to 3% by weight and a heavy hydrocarbon effluent, said heavy hydrocarbon effluent being an effluent containing at least 50% by weight of hydrocarbons comprising more than n carbon atoms, said process comprising the feeding of a reactive distillation section with said olefinic feedstock and the feeding of said reactive distillation section with an alcohol feedstock, said alcohol feedstock comprising at least one primary alcohol, characterized in that:

said reactive distillation section comprises a column comprising a column head reflux zone, an intermediate reaction zone comprising at least 6 reactive doublets, each reactive doublet comprising a catalytic bed followed by a separating theoretical plate, and a lower fractionation zone comprising between 5 and 25 theoretical plates, said reactive distillation section is operated at a relative column head pressure in the reflux zone of between 0.3 and 0.5 MPa, a column head temperature in the reflux zone of between 40° C. and 60° C. and a molar reflux ratio of between 1.8 and 2.2, said reactive section is fed with said olefinic feedstock in the fractionation zone of the column and with the alcohol feedstock in the reflux zone, such that the mole ratio of the primary alcohol introduced relative to the tertiary branched olefins, having a number of carbon atoms of less than or equal to (n+1), of the olefinic feedstock is between 0.8 and 1.1.

The Olefinic Feedstock

The olefinic feedstock treated by means of the process according to the invention is characterized by its high content of olefins. It advantageously contains at least comprising at least 70% by weight, preferentially at least 80% by weight, and even more preferably at least 90% by weight of linear and branched olefins, preferably of desired chain length, i.e. comprising n carbon atoms, n being an integer between 4 and 10, preferably between 4 and 8 and very preferably between 4 and 5. The high titer of olefins gives this cut particularly high reactivity, both in the downstream profitable exploitation steps and in the conversion or treatment steps to which it is subjected.

The branched olefins containing n carbon atoms comprise tertiary olefins containing n carbon atoms.

The olefinic feedstock treated according to the invention is a mixture of linear and branched olefins, the branched olefins being tertiary and non-tertiary branched olefins. The olefinic feedstock typically comprises at least 10% by weight, notably at least 15% by weight, of tertiary branched olefins, notably having a carbon number of less than or equal to (n+1), as a mixture with the linear olefins containing n carbon atoms, n having the abovementioned definition.

The olefins predominantly present in the feedstock are olefins containing n carbon atoms, n being an integer between 4 and 10, preferably between 4 and 8 and very preferably between 4 and 5. According to a preferred embodiment, the olefins predominantly present in the feedstock are olefins containing 4 carbon atoms, more particularly butenes. The olefinic feedstock to be treated notably comprises a mixture of n-butenes (1-butene and 2-butenes) and of branched olefins comprising tertiary branched olefins, such as isobutene and optionally other tertiary branched olefins containing at least 5 carbon atoms. The olefinic feedstock treated according to the invention is preferably a feedstock comprising at least 70% by weight, preferentially at least 80% by weight and even more preferably at least 85% by weight of said mixture of n-butenes and of branched olefins comprising tertiary branched olefins, and comprising at least 10% by weight, preferably at least 15% by weight and preferentially at least 20% by weight of tertiary branched olefins.

The olefinic feedstock treated according to the invention may also contain water and/or other hydrocarbon-based compounds (impurities). The hydrocarbon-based compounds may be paraffins, dienes and oxygen-based organic compounds, among which mention may be made of aldehydes, ketones, alcohols, acetals, ethers, esters, furans and carboxylic acids. The olefinic feedstock may also contain non-organic impurities, for example sodium salts.

Advantageously, the olefinic feedstock treated according to the invention is obtained from the isomerizing dehydration of alcohol, preferably of a monoalcohol, substituted in position 2 with an alkyl group and the hydroxyl group —OH of which is borne by a primary carbon atom. Preferably, the olefinic feedstock treated according to the invention is obtained from the isomerizing dehydration, advantageously on a zeolite catalyst of FER type preferably with an Si/Al mole ratio of less than 100, more preferentially between 8 and 70, of isobutanol or of a mixture of butanol isomers comprising isobutanol.

Reactive Distillation Section

The treatment process according to the invention comprises a reactive distillation section in which is performed the etherification of the tertiary branched olefins, in particular comprising a number of carbon atoms of less than or equal to n, n having the definition mentioned previously, for example isobutene and tertiary branched olefins containing 5 carbon atoms, included in the olefinic feedstock and the separation of the targeted linear olefins (i.e. linear olefins containing n carbon atoms) from the heavy compounds (impurities), comprising more than n carbon atoms, which may be included in the olefinic feedstock, and from the ethers formed.

According to the invention, the reactive distillation section comprises a column comprising a column head reflux zone, an intermediate reaction zone in which is found the catalytic beds, and a lower fractionation zone.

The reflux zone is composed of two or three theoretical plates. Advantageously, the reactive distillation section comprises, at the top of the column, a reflux system with at least one condenser and a return of the stream into the reflux zone of said column. The reflux systems that may be used in the process according to the invention are those that are well known to a person skilled in the art. Usually, the condenser is counted as theoretical plate 1 and the reflux is thus reintroduced into the column onto theoretical plate 2.

The intermediate reaction zone corresponds to the catalytic section, or reaction section, in which the etherification reaction takes place, notably between the tertiary branched olefins of the feedstock that it is desired to remove and the primary alcohol introduced into the column. According to the invention, the intermediate reaction zone comprises at least 6 reactive doublets, preferably between 6 and 12 reactive doublets and preferentially between 6 and 10 reactive doublets. A reactive doublet comprises a catalytic bed followed by a separating theoretical plate. The separating theoretical plate is located downstream of the catalytic bed in the direction of flow of the liquid. The catalytic doublet according to the invention may also comprise a distributing plate upstream of the catalytic bed.

According to the invention, a reactive doublet is counted as two theoretical stages (or theoretical plates).

Thus, according to the usual numbering, in the case of using a reflux system with a condenser, the first reactive doublet is located between theoretical plates 4 and 5 or 5 and 6, preferably between theoretical plates 5 and 6. The term "first reactive doublet" means the upper reactive doublet, i.e. the one adjacent to the reflux zone, and the term "last reactive doublet" means the lower reactive doublet, i.e. the one adjacent to the fractionation zone.

The catalytic bed comprises a catalyst, which is preferably acidic, in particular an acid catalyst in the Brønsted sense. The catalyst may be an ion-exchange resin, which is preferably acidic, and in particular a cation-exchange resin, preferably in its acid form. Advantageously, the catalyst is a proton-exchange resin, preferably a sulfonic acid resin, for instance a resin based on sulfonated styrene-divinylbenzene copolymer.

The lower fractionation zone comprises between 5 and 25 theoretical plates, preferably between 7 and 23 theoretical plates, preferentially between 10 and 15 theoretical plates.

Advantageously, the distillation section comprises a reboiling system located on the bottom side of the column and comprising, for example, a reboiler outside the column and a return of the effluent toward the bottom of the column. The reboiling systems that may be used in the process according to the invention are those that are well known to a person skilled in the art.

In accordance with the invention, the feeding of the reactive distillation section with olefinic feedstock to be treated is located in the fractionation zone of the column (lower zone of the column). Preferably, the feeding with olefinic feedstock to be treated is located in the upper third of the fractionation zone of the column. Even more preferably, the column is fed with the olefinic feedstock at the level of the second theoretical plate below the last reactive doublet.

According to the invention, the reactive distillation section is fed with an alcohol feedstock comprising at least one primary alcohol, advantageously in liquid form, at the level of the reflux zone of the column. The alcohol feedstock comprises a primary alcohol, preferably chosen from ethanol and methanol. Said alcohol feedstock comprises at least 20% by weight, preferentially at least 30% by weight, preferentially at least 35% by weight and preferably at least 40% by weight of primary alcohol. The alcohol feedstock comprises up to 99% by weight, preferably up to 99.9% by weight, very preferentially up to 100% by weight of primary alcohol. Said alcohol feedstock is low in water; it comprises from 0 to 50% by weight of water. Said alcohol feedstock may also comprise impurities such as aldehydes, ketones or acids, the content of which represents not more than 1% by weight of said alcohol feedstock, and hetero elements such as Na, K, Al and Fe in ionic form in a content of less than 500 ppm, preferentially less than 100 ppm, these hetero elements having a negative effect on the lifetime of the catalysts, in particular of the ion-exchange resins advantageously used in the process according to the invention.

In a preferred embodiment, the alcohol feedstock comprises ethanol, preferably in a content of greater than or equal to 35% by weight, in particular in a content of between 35% and 99% by weight, preferentially between 35% and 99.9% by weight, relative to the total weight of the alcohol feedstock. Said alcohol feedstock comprising ethanol may also advantageously comprise between 0 and 50% by weight of water, a content of alcohols other than ethanol, for instance methanol, butanol and/or isopentanol, of less than 10% by weight, and preferably less than 5% by weight, a content of oxygen-based compounds other than alcohols, for instance ethers, acids, ketones, aldehydes and/or esters, of less than 1% by weight, and a content of organic and mineral nitrogen and sulfur of less than 0.5% by weight, the weight percentages being expressed relative to the total weight of said alcohol feedstock.

According to this preferred embodiment, the alcohol feedstock may optionally be obtained via an alcohol synthesis process starting with fossil resources, for instance starting with coal, natural gas or carbon-based waste. It may also advantageously originate from non-fossil resources. Preferably, the alcohol feedstock comprising ethanol is produced from a renewable source derived from biomass, often referred to as "bioethanol". Bioethanol is a feedstock produced by biological means, preferably by fermentation of sugars obtained, for example, from sugar-yielding plant crops such as sugarcane (saccharose, glucose, fructose and sucrose), from beetroot, or from starchy plants (starch) or from lignocellulosic biomass or from hydrolysed cellulose (predominantly glucose and xylose, galactose), containing variable amounts of water. For a more complete description of the conventional fermentation processes, reference may be made to the publication "Les Biocarburants, État des lieux, perspectives et enjeux du développement [Biofuels, current state, perspectives and development challenges]", Daniel Ballerini, published by Technip. Said alcohol feedstock may also advantageously be obtained from synthesis gas. Said alcohol feedstock may likewise also advantageously be obtained from hydrogenation of the corresponding acids or esters. In this case, acetic acid or acetic esters are advantageously hydrogenated using hydrogen into ethanol. Acetic acid may advantageously be obtained by carbonylation of methanol or by fermentation of carbohydrates.

Preferably, the alcohol feedstock comprising ethanol is produced from a renewable source derived from biomass.

According to the invention, the reactive distillation section is fed with an alcohol feedstock comprising at least one primary alcohol, such as methanol or ethanol, preferably ethanol, advantageously in liquid form, at the level of the reflux zone of the column. The alcohol feedstock is preferably introduced at the level of the downstream theoretical plate adjacent to the reflux plate, i.e. at the level of theoretical plate 3 according to the usual numbering and with the use of a reflux system with a condenser (theoretical plate 1) and return of the reflux to theoretical plate 2.

The amount of alcohol feedstock comprising at least one primary alcohol introduced into the column is such that the mole ratio of said primary alcohol introduced relative to the tertiary branched olefins of the olefinic feedstock containing a number of carbon atoms of less than or equal to (n+1), n being an integer between 4 and 10, as defined previously, is between 0.8 and 1.1, preferably between 0.9 and 1.1 and preferentially between 0.9 and 1.0.

In a particular embodiment of the invention in which the olefinic feedstock is a mixture of linear butenes (1-butene, 2-butene) and of branched olefins notably comprising isobutene, the amount of alcohol feedstock introduced into the column is such that the mole ratio of said primary alcohol, preferably ethanol, of the alcohol feedstock introduced, relative to the isobutene and to the tertiary branched olefins containing 5 carbon atoms of the olefinic feedstock is between 0.8 and 1.1, preferably between 0.9 and 1.1 and preferentially between 0.9 and 1.0.

The primary alcohol of the alcohol feedstock reacts with the tertiary branched olefins containing n carbon atoms and the lighter tertiary branched olefins having a carbon number of less than n, n having the definition mentioned previously. The primary alcohol may also react with the tertiary branched olefins containing (n+1) carbon atoms, which may be present in the olefinic feedstock, preferably in low content, for instance in a mass content of less than or equal to 5% relative to the mass of the olefinic feedstock.

In the case of an olefinic feedstock comprising a mixture of linear butenes and of branched olefins notably comprising isobutene, the primary alcohol of the alcohol feedstock may react with, besides isobutene, the tertiary branched C5 olefins, i.e. the tertiary branched olefins containing 5 carbon atoms, which may be present in the olefinic feedstock to be treated. These tertiary branched C5 olefins may in fact be entrained toward the reaction section where they can react with the primary alcohol to form an ether. The tertiary or non-tertiary branched olefins with a higher carbon number (i.e. 6 carbon atoms and more, C6+) are, themselves, entrained into the fractionation zone of the column and will be extracted with the heavy hydrocarbon effluent at the bottom of the column. Thus, the mole ratio between the primary alcohol, preferably ethanol, of the alcohol feedstock introduced, and the combination consisting of isobutene and of the tertiary branched C5 olefins of the olefinic feedstock is between 0.8 and 1.1, preferably between 0.9 and 1.1 and preferentially between 0.9 and 1.0. The amount of primary alcohol introduced may also be adjusted relative to the amount of isobutene in the olefinic feedstock, to a mole ratio between the primary alcohol and the isobutene of between 0.9 and 1.1, preferably between 0.95 and 1.05 and even more preferably between 1.0 and 1.05.

The content of tertiary or non-tertiary branched olefin(s) of the feedstock is determined by any method known to a person skilled in the art, for example by gas chromatography. These same analytical methods are used to confirm the content of tertiary branched olefins in the olefinic effluent extracted at the top of the column of the process according to the invention.

In the particular embodiment of the invention in which the process according to the invention is integrated into a process for the isomerizing dehydration of an alcohol containing n carbon atoms, n being an integer between 4 and 10 as defined previously, substituted in position 2 with an alkyl group and the hydroxyl group —OH of which is borne by a primary carbon atom, into olefins containing n carbon atoms, for instance the process for the isomerizing dehydration of isobutanol into butenes, the content of tertiary branched olefins, such as isobutene and optionally of tertiary branched olefins containing 5 carbon atoms, in the olefinic raffinate leaving the reaction section of the isomerizing dehydration process (raffinate which constitutes the olefinic feedstock of the reactive distillation section according to the present invention) is determined on a sample taken upstream of the reactive distillation section according to the present invention, preferably upstream of a possible device for vaporizing said olefinic raffinate.

Advantageously, the olefinic feedstock to be treated which feeds the reactive distillation section is in liquid form or in gaseous form, preferably in gaseous form. The alcohol feedstock comprising the primary alcohol is, itself, advantageously introduced into the column in liquid form. In one preferred embodiment of the invention, the olefinic feedstock is in gaseous form and the alcohol feedstock comprising the primary alcohol is in liquid form. Thus, the liquid alcohol feedstock will pass in a descending motion in the column through the entire reaction section, becoming spread in each catalytic bed, in which beds the primary alcohol that it contains will react notably with the branched olefin of the feedstock.

According to the invention, the reactive distillation section is operated at a relative column head pressure of between 0.3 and 0.5 MPa, preferably between 0.35 and 0.40 MPa, at a column head temperature of between 40° C. and 60° C., preferably between 45° C. and 55° C., with a molar reflux ratio of between 1.8 and 2.2, preferably between 1.9 and 2.1.

These specific operating conditions make it possible to maintain the temperature in the reaction section in the optimum temperature range for the etherification reaction, i.e. between 60° C. and 80° C., preferably between 60° C. and 75° C. When the temperature in the reaction section exceeds this optimum temperature, the degree of conversion of the etherification reaction decreases and the risks of oligomerization of the branched olefins in the presence of the acid catalyst increase. When the temperature in the reaction section is below this optimum temperature, the degree of conversion of the etherification reaction remains low and the concentration of tertiary branched olefins in the olefinic effluent extracted at the top increases.

Under these operating conditions and with such column characteristics, the maximum content of 3% by weight of tertiary branched olefins (such as isobutene) in the olefinic effluent recovered at the top may be reached with limited losses of primary alcohol introduced, advantageously primary alcohol losses of less than or equal to 15% by weight, preferably less than or equal to 10% by weight. Under these conditions and with such column characteristics, the yield of the reaction section is, in point of fact, optimal and the ether formed is extracted in the heavy hydrocarbon effluent at the bottom of the column with the hydrocarbon-based impurities that may be contained in the feedstock. The olefinic effluent extracted at the top, which meets the specifications in terms of content of tertiary branched olefins (less than or equal to 3% by weight), can then be used as reagent in a metathesis unit.

In addition, the specific operating conditions of the invention, in particular in terms of specific pressure and temperature, and also the particular characteristics of the column make it possible to limit the oligomerization of the branched olefins, notably the tertiary olefins, and the degradation of the catalyst, notably of the ion-exchange resin, thus reducing the risk of premature fouling of the reactive distillation column.

Advantageously, the process according to the invention is integrated into a process for converting alcohols into olefins. The process according to the invention is more particularly integrated into the process for the isomerizing dehydration of butanol, more precisely of isobutanol, alone or as a mixture with the other butanol isomers, into butenes as a step of treatment of the olefinic raffinate obtained from the conversion reactor.

In the particular embodiment of the invention in which the olefinic feedstock to be treated according to the process of the invention comprises a mixture of n-butenes and of tertiary branched olefins, notably isobutene, and the primary alcohol introduced into the reactive distillation column is ethanol, one of the ethers formed is ethyl tert-butyl ether (or ETBE).

Advantageously, the olefinic effluent extracted at the top of the column, which may comprise primary alcohol introduced as etherification reagent, can be treated to remove said primary alcohol, for example by washing with water, notably in a liquid-liquid contactor operating, for example, at a relative pressure of 1 MPa and a temperature of between 20 and 40° C.

The examples that follow are presented for illustrative purposes and are nonlimiting.

FIGURE(S)

FIG. 1: Scheme of the reactive distillation section of the process according to the invention, said reactive distillation section comprising a reflux zone at the top of the column into which is introduced the reflux (4), an intermediate reaction zone (5) comprising at least 6 reactive doublets and a lower fractionation zone (6) comprising between 5 and 25 theoretical plates, said reactive distillation section being fed with the olefinic feedstock (1) in the fractionation zone (6) of the column and with the alcohol feedstock in the reflux zone of the column, the olefinic effluent (3) being extracted at the top of the column and the heavy hydrocarbon effluent (7) at the bottom of the column.

EXAMPLES

The examples that follow are based on process simulations integrating thermodynamic data matching experimental points (binary liquid-vapor equilibrium data, liquid-liquid partition coefficient and degree of conversion of the etherification reaction as a function of the operating conditions).

Example 1 (in Accordance)

An olefinic feedstock, obtained from the dehydration of isobutanol, comprising 21.8% by weight of isobutene and 2.15% of tertiary branched C5 olefins, feeds, in gaseous form, a reactive distillation column including 42 theoretical plates in total and equipped with a reflux system with a condenser. A stream of ethanol (EtOH) in liquid form is injected into the column in the reflux zone, on theoretical plate 3. The catalyst used is a sulfonic acid resin, Amberlyst® 15, sold by Dow.

Several tests are performed, varying a few parameters, in particular the localization of the feed on the column and the number of reactive doublets. The column characteristics and the operating conditions are summarized in Table 1.

Table 1 also relates, for each test performed, the results obtained in terms of content of tertiary branched C4 olefins (i.e. olefins containing 4 carbon atoms, i.e. isobutene) and C5 olefins of the effluent recovered at the top and the total losses of ethanol. The ethanol losses (weight %) are calculated in the following manner:

$$100 \times \frac{(\text{amount of ethanol in the top effluent}) + (\text{amount of ethanol in the bottom heavy hydrocarbon effluent})}{(\text{amount of ethanol introduced})}$$

It is seen from Table 1 that the objective as regards the content of isobutene tertiary branched olefins and tertiary branched C5 olefins (less than or equal to 3% by weight) in the effluent extracted at the top is achieved, irrespective of the parameters used, and for limited ethanol losses (<10% by weight).

TABLE 1

Column characteristics, operating conditions used and performance obtained (content of tertiary branched C4 and C5 olefins of the olefinic effluent and ethanol losses)

| | Test 1 (in accordance) | Test 2 (in accordance) | Test 3 (in accordance) |
|---|---|---|---|
| Isobutene content of the feedstock (weight %) | 21.8% | 21.8% | 21.8% |
| Tertiary branched C5 olefins content of the feedstock (weight %) | 2.15 | 2.15 | 2.15 |
| Total number of theoretical plates | 42 | 42 | 42 |
| Number of reactive doublets | 6 | 8 | 10 |
| Catalyst | Amberlyst® 15 | Amberlyst® 15 | Amberlyst® 15 |
| First/last theoretical plate of the reaction section | 5/16 | 5/20 | 5/24 |

TABLE 1-continued

Column characteristics, operating conditions used and performance obtained (content of tertiary branched C4 and C5 olefins of the olefinic effluent and ethanol losses)

| | Test 1 (in accordance) | Test 2 (in accordance) | Test 3 (in accordance) |
|---|---|---|---|
| Number of theoretical plates in the fractionation zone | 25 | 21 | 17 |
| EtOH injection theoretical plate* | 3 | 3 | 3 |
| Feedstock injection theoretical plate* | 18 | 22 | 26 |
| EtOH/isobutene mole ratio | 1.025 | 1.025 | 1.025 |
| EtOH/tertiary branched C4 and C5 olefins mole ratio | 0.95 | 0.95 | 0.95 |
| Relative head pressure (MPa) | 0.37 | 0.37 | 0.37 |
| Head temperature (° C.) | 50 | 50 | 50 |
| Molar reflux ratio | 2.06 | 1.97 | 1.97 |
| Tertiary branched C4 and C5 i olefins content of the effluent (weight %) | <3% | <3% | <3% |
| EtOH losses (weight %) | <10% | <10% | <10% |

*the theoretical plates being numbered in the direction of flow of the liquid in the column, i.e. from the top to the bottom of the column, the condenser being counted as plate 1, the reflux being injected at plate 2

Table 2 collates the mass compositions of the feedstock and of the olefinic effluent extracted at the top in the case of test 2.

Table 2 shows that the content of tertiary branched olefins (2.76% by weight), i.e. of isobutene and tertiary branched C5 olefins, in the head olefinic effluent less than 3% by weight relative to the total weight of the olefinic effluent.

From Table 2, it is also seen that the column allows good separation of the butenes from the heavy hydrocarbon compounds (impurities) contained in the feedstock. Specifically, the hydrocarbon impurities, which represent 10.57% by weight of the olefinic feedstock, represent no more than 0.3% in the olefinic effluent recovered at the top (the ethanol introduced as alcohol feedstock is not counted).

TABLE 2

Mass compositions of the olefinic feedstock and of the olefinic effluent extracted at the top

| Compositions (weight %) | FEEDSTOCK | EFFLUENT |
|---|---|---|
| Cis-2-BUTENE | 21.34 | 30.02 |
| Trans-2-BUTENE | 30.56 | 43.19 |
| 1-BUTENE | 15.56 | 22.04 |
| ISOBUTENE | 21.80 | 2.76 |
| H2O | 0.16 | 0.23 |
| ETHANOL | 0.00 | 1.47 |
| ACETIC ACID | 0.35 | 0.00 |
| TERTIARY BRANCHED C5 OLEFINS | 2.15 | 0.00 |
| ISOBUTANAL | 0.07 | 0.00 |
| BUTANOL | 0.01 | 0.00 |
| s-BUTANOL | 0.04 | 0.00 |
| t-BUTANOL | 0.03 | 0.00 |
| i-BUTANOL | 2.36 | 0.00 |
| 2,3,3-TRIMETHYL-1-BUTENE | 0.54 | 0.00 |
| 2,4,4-TRIMETHYL-1-PENTENE | 4.26 | 0.00 |
| ETBE | 0.00 | 0.00 |
| OTHER HYDROCARBONS | 0.76 | 0.29 |

Example 2 (not in Accordance)

Introduction of Ethanol into the Feedstock Upstream of the Column

An olefinic feedstock, obtained from the dehydration of isobutanol, comprising 21.8% by weight of isobutene and 2.15% by weight of tertiary branched C5 olefins, is treated by means of a process involving a reactive distillation column. A stream of ethanol is introduced into the feedstock upstream of the reactive distillation column. The catalyst used is a sulfonic acid resin, Amberlyst® 15, sold by Dow.

Table 3 collates the parameters used (column characteristics and operating conditions) and the performance of the reactive distillation section in terms of isobutene content of the olefinic effluent extracted at the top and ethanol losses.

The content of tertiary branched C4 and C5 olefins in the head effluent is equal to 23.4% by weight. It is thus much higher than the targeted objective (less than or equal to 3% by weight). The ethanol losses are also very high (90.0% by weight). The tertiary branched olefins of the feedstock were virtually not converted into ethers and were thus not able to be separated from the linear butenes when the ethanol is introduced into the column with the feedstock.

TABLE 3

Column characteristics, operating conditions used and performance obtained (content of tertiary branched C4 and C5 olefins of the olefinic effluent and ethanol losses)

| | Test not in accordance |
|---|---|
| Isobutene content of the feedstock (weight %) | 21.8% |
| Tertiary branched C5 olefins content of the feedstock (weight %) | 2.15 |
| Total number of theoretical plates | 42 |
| Number of reactive doublets | 8 |
| Catalyst | Amberlyst® 15 |
| First/last theoretical plate of the reaction section | 5/20 |
| Number of theoretical plates in the fractionation zone | 21 |
| Injection of EtOH | into the feedstock |
| Feedstock injection theoretical plate* | 22 |
| EtOH/isobutene mole ratio | 1.025 |
| EtOH/tertiary branched C4 and C5 olefins mole ratio | 0.95 |
| Relative head pressure (MPa) | 0.37 |
| Head temperature (° C.) | 47 |
| Molar reflux ratio | 1.97 |
| Tertiary branched C4 and C5 olefins content of the effluent (weight %) | 23.4% |
| EtOH losses (weight %) | 90.0% |

*the theoretical plates being numbered in the direction of flow of the liquid in the column, i.e. from the top to the bottom of the column, the condenser being counted as plate 1, the reflux being injected at plate 2

Example 3 (not in Accordance)

Several Relative Column Head Pressures not in Accordance with the Present Invention are Tested.

An olefinic feedstock, comprising 21.8% by weight of isobutene and 2.15% of tertiary branched C5 olefins, is injected into the reactive distillation column in gaseous form. A stream of ethanol, in liquid form, is introduced into the column at the level of the reflux zone. The catalyst used is a sulfonic acid resin, Amberlyst® 15, sold by Dow.

Table 4 collates the column characteristics, the operating conditions used and the performance of the reactive distillation section (content of tertiary branched C4 and C5 olefins of the head effluent and ethanol losses).

TABLE 4

Column characteristics, operating conditions and performance obtained (content of tertiary branched C4 and C5 olefins of the olefinic effluent and ethanol losses)

|  | Test a (not in accordance) | Test b (not in accordance) |
|---|---|---|
| Isobutene content of the feedstock (weight %) | 21.8% | 21.8% |
| Tertiary branched C5 olefins content of the feedstock (weight %) | 2.15 | 2.15 |
| Total number of theoretical plates | 42 | 42 |
| Number of reactive doublets | 8 | 8 |
| Catalyst | Amberlyst ® 15 | Amberlyst ® 15 |
| First/last theoretical plate of the reaction section | 5/20 | 5/20 |
| Number of theoretical plates in the fractionation zone | 21 | 21 |
| EtOH injection theoretical plate* | 3 | 3 |
| Feedstock injection theoretical plate* | 22 | 22 |
| EtOH/isobutene mole ratio | 1.025 | 1.025 |
| EtOH/tertiary branched C4 and C5 olefins mole ratio | 0.95 | 0.95 |
| Relative head pressure (MPa) | 0.29 | 0.7 |
| Column head temperature (° C.) | 43 | 71 |
| Molar reflux ratio | 1.97 | 2.02 |
| Min/max temperatures in the catalytic section | 43/74 | 75/85 |
| Tertiary branched C4 and C5 olefins content of the effluent (weight %) | 3.07% | >3.0% |
| EtOH loss (weight %) | <10% | 12% |

*the theoretical plates being numbered in the direction of flow of the liquid in the column, i.e. from the top to the bottom of the column, the condenser being counted as plate 1, the reflux being injected at plate 2

From Table 4, when the relative column head pressure is low (0.29 MPa), the content of tertiary branched C4 and C5 olefins in the effluent extracted at the top is greater than 3% (3.07%). When the relative column head pressure is low, the conversion of the tertiary branched olefins into ethers is insufficient to allow efficient separation and consequently to achieve a content of tertiary branched olefins of less than or equal to 3% by weight in the head olefinic effluent.

When the relative column head pressure is high (0.7 MPa), greater than 0.5 MPa, the temperature in the reaction section varies and becomes higher than 80° C. Beyond this temperature, the etherification reaction is no longer optimal and the unconverted tertiary branched olefins become readily oligomerized on contact with the acid catalyst. Thus, the ethanol is less consumed, leading to increased ethanol losses. The content of tertiary branched olefins in the olefinic effluent also increases.

The invention claimed is:

1. A process for treating, by reactive distillation, an olefinic feedstock comprising linear olefins containing n carbon atoms, n being an integer between 4 and 10, and branched olefins, the branched olefins comprising tertiary branched olefins, so as to produce an olefinic effluent with a mass content of tertiary branched olefins of less than or equal to 3% by weight and a heavy hydrocarbon effluent, said heavy hydrocarbon effluent being an effluent comprising at least 50% by weight of hydrocarbons comprising more than n carbon atoms, said process comprising the feeding of a reactive distillation section with said olefinic feedstock and the feeding of said reactive distillation section with an alcohol feedstock, said alcohol feedstock comprising at least one primary alcohol, characterized in that:

said reactive distillation section comprises a column comprising a column head reflux zone, an intermediate reaction zone comprising at least 6 reactive doublets, each reactive doublet comprising a catalytic bed followed by a separating theoretical plate, and a lower fractionation zone comprising between 5 and 25 theoretical plates, said reactive distillation section is operated at a relative column head pressure in the reflux zone of between 0.3 and 0.5 MPa, a column head temperature in the reflux zone of between 40° C. and 60° C. and a molar reflux ratio of between 1.8 and 2.2, said reactive distillation section is fed with said olefinic feedstock in the fractionation zone of the column and with alcohol feedstock in the reflux zone, such that the mole ratio of the primary alcohol introduced relative to the tertiary branched olefins, having a number of carbon atoms of less than or equal to (n+1), of the olefinic feedstock is between 0.8 and 1.1.

2. The process as claimed in claim 1, in which the olefinic feedstock comprises a mixture of n-butenes and of branched olefins comprising isobutene and tertiary branched olefins containing 5 carbon atoms.

3. The process as claimed in claim 1, in which the column head reflux zone is composed of two or three theoretical plates.

4. The process as claimed in claim 1, in which the intermediate reaction zone comprises between 6 and 12 reactive doublets.

5. The process as claimed in claim 1, in which the catalytic bed comprises a cation-exchange resin.

6. The process as claimed in claim 1, in which the lower fractionation zone comprises between 7 and 23 theoretical plates.

7. The process as claimed in claim 1, in which the feeding with said olefinic feedstock is located in the upper third of the fractionation zone.

8. The process as claimed in claim 1, in which the olefinic feedstock is in gaseous form and the alcohol feedstock is in liquid form.

9. The process as claimed in claim 1, in which the primary alcohol of the alcohol feedstock introduced into the column reflux zone is ethanol.

10. The process as claimed in claim 1, in which the mole ratio of primary alcohol introduced relative to the tertiary branched olefins with a number of carbon atoms of less than or equal to (n+1) of the olefinic feedstock is between 0.9 and 1.0.

11. The process as claimed in claim 1, in which the relative column head pressure in the reflux zone is between 0.35 and 0.40 MPa.

12. The process as claimed in claim 1, in which the column head temperature in the reflux zone is between 45° C. and 55° C.

13. The process as claimed in claim 1, in which the molar reflux ratio is between 1.9 and 2.1.

14. A process for the isomerizing dehydration of a feedstock comprising from 40% to 100% by weight of an alcohol substituted in position 2 with an alkyl group and the hydroxyl group —OH of which is borne by a primary carbon atom, said dehydration process comprising at least one step of converting said substituted alcohol into olefins and a step involving the process as claimed in claim 1 for treating the olefinic raffinate produced in the conversion step.

* * * * *